United States Patent [19]
Albarella et al.

[11] Patent Number: 5,212,066
[45] Date of Patent: May 18, 1993

[54] USE OF INHIBITORS OF COLOR GENERATION IN CHROMOGENIC ASSAYS

[75] Inventors: James P. Albarella, Granger; Todd K. Cast, South Bend; David W. Michaels, Elkhart; Wallace G. Strycker, Goshen, all of Ind.

[73] Assignee: Miles Inc., Elkhart, Ind.

[21] Appl. No.: 791,380

[22] Filed: Nov. 14, 1991

[51] Int. Cl.$^5$ ............................ C12Q 1/54; C12Q 1/28
[52] U.S. Cl. ........................................ 435/28; 435/14; 435/27; 435/10; 435/805
[58] Field of Search ...................... 435/28, 14, 27, 805, 435/10; 514/248, 826, 363, 364

[56] References Cited

U.S. PATENT DOCUMENTS 4,220,713  9/1980  Rittersdorf et al. .................. 435/14

OTHER PUBLICATIONS

G. R. Schonbaum, J. Biol. Chem. 248 (1973) 502–511 "New Complexes of Peroxidases with Hydroxamic Acids, Hydrazides, and Amides".

Hidaka, H. et al. Arch. Biochem. Biophys. 140, (1970) 174–180—"Evidence of a Hydrazine-Reactive Group at the Active Site of the Nonheme Portion of Horseradish Peroxidase".

Morrison et al; "Organic Chemistry"; 3rd Edition; pp. 366–367 (1973).

Usmani et al; "Chemical Abstracts"; 112(19):17524p (1989).

*Primary Examiner*—Ronald W. Griffin
*Assistant Examiner*—Louise N. Leary
*Attorney, Agent, or Firm*—Jerome L. Jeffers

[57] ABSTRACT

Disclosed is a novel diagnostic reagent system for the detection of hydroperoxides or substances which react with peroxidatively active substances resulting in the liberation of hydroperoxides which reagent system comprises a chromogenic oxidation indicator and a peroxidase or a peroxidatively active substance, together with an inhibitor of color generation selected from the group of 1,4-disubstituted semicarbazides, thiosemicarbazides and 1,5-disubstituted carbazides as inhibitors of color generation. By inhibiting the generation of color formed by oxidation of the chromogenic indicator, the indicator's usefulness in discriminating between varying concentrations of analyte is enhanced.

24 Claims, No Drawings

USE OF INHIBITORS OF COLOR GENERATION IN CHROMOGENIC ASSAYS

BACKGROUND OF THE INVENTION

The present invention is concerned with a process for the semi-quantitative determination of hydroperoxides or substances which react with peroxidatively active substances to liberate hydroperoxides in aqueous fluids and with a chromogenic oxidation indicator/color generation inhibitor system which extends the useful range of test systems employing such reagents.

The determination of glucose in body fluids, such as urine or blood, is of importance not only in the case of diabetic patients who must control their sugar input, but also in those situations in which the detection of disease as a public health measure requires the screening of the urine or blood of large numbers of people. Because early diagnosis and continued control are so important in diabetes, a glucose test, to be of greatest value to the patient in monitoring and controlling the disease, must be conveniently rapid, simple enough to serve the needs of the patient and sensitive enough to reflect meaningful variations in urine or blood glucose.

The use of glucose oxidase, a peroxidatively active substance [POD] and a chromogenic oxidation indicator [IND], which is oxidized upon exposure to hydrogen peroxide in the presence of the peroxidatively active substance for the detection of glucose in urine is known. The system involves the formation of hydrogen peroxide by the action of glucose oxidase on glucose:

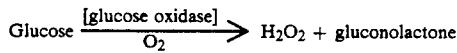

and the resultant oxidation of the indicator [Ind] to its oxidized state [Ind]$_{ox}$ in the presence of a peroxidase which is visually detectable by a color change:

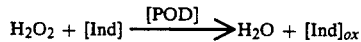

The test described above can be used in the determination of a series of materials which react with oxygen and an oxidase resulting in the formation of hydrogen peroxide. Thus, the system is useful for the detection of occult blood in various body tissues because of the fact that hemoglobin is such a material. In addition, such a system is useful for the detection of cholesterol, triglycerides and uric acid.

Many indicators in these reagent systems are selected to generate color at wavelengths free from endogenous interferents such as bilirubin and hemoglobin to produce a chromogen of high color intensity or extinction. This is especially true in the case of benzidine based indicators such as benzidine, o-tolidine and o-dianisidine as well as the substituted benzidine chromogenic indicators such as 3,3',5,5'-tetramethylbenzidine, 3,3'-diaminobenzidine and 3,3'-dimethoxybenzidine. This property makes them valuable in the detection of micromolar to nanomolar concentration levels of analytes frequently encountered in clinical chemistry and immunochemistry. Unfortunately, significant problems can be encountered in adapting these oxidative indicator systems to the detection of analytes present in higher concentration, especially in situations where sample dilution is undesirable because of instrument or format limitations. Under these conditions, it is often found that too much color intensity is developed at low analyte concentrations making subsequent higher, and in many cases more clinically significant, analyte concentrations more difficult to detect accurately because of limitations in discerning increasingly darker shades of the produced color. This is especially true in the case of the substituted benzidine indicators mentioned above because these indicators quickly turn from light yellow to dark blue/black when used in the determination of relatively high amounts of glucose in urine.

The above described problems are exemplified in the design of test systems for the dry phase detection of urine glucose where concentrations of 0.1 to 5 g/dL are typically observed. Dry phase test systems for this analyte are designed to be detected both visually and instrumentally using reflectance spectroscopy. As is demonstrated in the subsequent examples, most of the maximum color intensity can be produced at the first clinically significant analyte level of interest, making it difficult to visually detect subsequent analyte levels. In addition, reagents stored under elevated temperature conditions, i.e. subjected to thermal stress, frequently exhibit deteriorated color development resulting in assay imprecision.

Aside from the previously mentioned benzidine based indicators, this problem is also encountered with other chromogenic indicator systems which form blue colors upon oxidation such as guaiacol, reduced (leuco or dihydro) 2,6-dichlorophenolindophenol 2,2'-azineobis-(3-ethylbenzothiazoline-6-sulfonic acid), 1-methylbenzothiazol-2-one hydrazone with 3-N,N-dimethylaminobenzoic acid or N,N-Bis-(2-hydroxyethyl)aniline or related coupler systems.

The literature contains references to the use of certain reagents, e.g. hydrazine, hydrazide and hydroxamic acid derivatives, to inhibit the action of horseradish peroxidase (HRP) by complex formation and, in some cases, covalent binding. Thus, it is disclosed in J. Biol. Chem. 248 (1973), 502 that the association and inhibition of HRP was competitive, i.e. could be decreased by adding hydrogen donors such as phenol, aniline and hydroquinone. In Arch. Biochem. Biophys. 140 (1970), 174 there is disclosed a procedure in which the color resulting from the HRP catalyzed reaction of H$_2$O$_2$ with o-dianisidine was used to determine the residual activity of the partially deactivated HRP. In U.S Pat. No. 4,220,713 there is disclosed a diagnostic agent for the detection of hydroperoxides or of substances which react with the liberation of hydroperoxides containing a stabilized oxidation indicator wherein the stabilizer is a 1-arylsemicarbazide of the formula:

in which Ar is aryl or aryl substituted with alkyl, alkoxy or halogen.

Semicarbazides which are substituted at the 1 and 4 positions are known. Thus, 4-methyl-1-phenyl semicarbazide is reported in C.A. 30, 48359, Rec. Trav. Chim. 55, 101–21 (1936) and 4-allyl-1-phenylsemicarbazide is reported in C.A. 69, 14270, Appl. Spectrosc. 22, 167–69 (1968). Likewise, there are reported 4-benzyl-1-phenylsemicarbazide in C.A. 5, 17779, Chem. Ber. 44, 560–83 (1911); 4-phenyl-1-dimethylsemicarbazide in C.A. 60, P2950, Fr. Patent 1,334,586. Another 1,4 disubstituted semicarbazide, 4-phenyl-1-(2 pyridyl)semicarbazide is reported in C.A. 57, 12435, J. Chem. Eng. Data, 12 (4), 612–615 (1967).

SUMMARY OF THE INVENTION

The present invention involves a diagnostic reagent system for the detection of analytes which are hydroperoxides or substances which react with peroxidatively active substances resulting in the liberation of hydroperoxides. The reagent system comprises a buffer, a chromogenic oxidation indicator, an oxidase selective for the analyte to be detected and a peroxidase or a peroxidatively active substance together with an inhibitor of color generation. The inhibitor of color generation is selected from the group of 1,4-disubstituted semicarbazides, 1,4-disubstituted thiosemicarbazides and 1,5-disubstituted carbazides and thiocarbazides characterized by the formula:

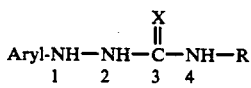

where X is oxygen or sulfur, R is alkyl of 1 to 6 carbon atoms, benzyl, aryl or NH-aryl$_2$ where aryl$_2$ can be the same as or different than aryl. The inhibitor is selected from those materials which inhibit the formation of color by the indicator thereby reducing color intensity at the initial analyte concentration and distributing it instead across two or more higher analyte concentrations, thereby facilitating visual and instrumental color discrimination between differing levels of analyte in the aqueous system.

DESCRIPTION OF THE INVENTION

The diagnostic reagent of the present invention is normally used to semiquantitatively determine the presence of hydroperoxides or substances which react with the liberation of hydroperoxides in a liquid environment. Typical analytes include, for example; glucose, cholesterol, triglycerides and uric acid. For purposes of this invention, the term "fluids" is intended to include body fluids such as blood serum, blood plasma, urine, spinal fluids and aqueous solutions containing urea. Although the preferred application of the test means and process of this invention is to body fluids, such as blood and urine, it should be understood that the disclosed test means and process can be applied to industrial fluids as well.

The diagnostic reagent system of this invention can be used in the form of a treated paper, a bottled reagent, a frangible capsule containing the agent which can be dropped into the fluid being tested or a solid gel.

A preferred means of using the reagent system is to treat a suitable carrier matrix with the chromogen, the oxidase selective for the analyte, the peroxidatively active substance and the inhibitor in the form of its buffered aqueous solution. The expression "carrier matrix" refers to either bibulous or nonbibulous matrices which are insoluble in and maintain their structural integrity when exposed to water or other physiological fluids. Suitable bibulous matrices which can be used include paper, cellulose, wood, synthetic resin fleeces, woven and nonwoven fabrics and the like. Non-bibulous matrices include glass fiber and organo-polymeric materials, such as polypropylene or nylon. The carrier matrix can be coated, soaked, immersed in, sprayed or printed with the liquid reagent composition and thereafter dried by suitable means such as ambient or forced air drying to leave the dry reagent/matrix combination. The matrix can advantageously be affixed to an insoluble support member such as an organoplastic strip, e.g., polystyrene, such as by use of a double faced adhesive tape, for ease of use.

When the reagent is to be used for determining the amount of glucose in a body fluid such as urine or blood, glucose oxidase is normally incorporated into the matrix to provide a unitary test device which, when contacted with a fluid containing glucose, will liberate hydrogen peroxide thereby causing the oxidative chromogen to undergo a color change.

In this embodiment, a typical reagent composition for use in treating the carrier matrix will contain from 25 to 1,000 international units (I.U.) of glucose oxidase per mL and from 20 to 1,000 I.U. of peroxidatively active substance (typically horseradish peroxidase) per mL. The amount of chromogen and inhibitor will vary depending on the particular chromogen selected, the particular color inhibitor therefor and whether the test device is to be used to test for low or high levels of glucose. In the case of substituted benzidines such as 3,3',5,5'-tetramethyl benzidine (TMB) the reagent composition will contain from 5 to 30 mg/mL indicator. The color inhibitor of the present invention will be included in an amount of from 5 to 60 mg/mL when the test device is to be used for the determination of high amounts of glucose, i.e. from about 1 to 5 g/dL and from 0.1 to 6.0 mg/mL in the case of a test device to be used for detecting low amounts of glucose, i.e. from about 0.1 to 1.0 g/dL. The preferred amounts of other chromogens and color inhibitors can be readily determined by routine experimentation. This composition can either be used as is in the case of a liquid assay or adsorbed into the previously mentioned matrix system to provide a dry assay device.

Most of the color inhibitors useful in the present invention have been found to be suitable for use in reagent systems for detecting both low and high concentrations of glucose in fluids by adjusting the concentration thereof. Thus, in the case of our preferred color inhibitor, 4-allyl-1-(4-chlorophenyl)semicarbazide, there will preferably be a concentration of from 50 to 200 mM present in the liquid reagent when it is to be used for the detection of high levels of glucose and from 1 to 15 mM when low levels of glucose are present. Those inhibitors that can be used in reagents for detecting both low and high concentrations of glucose in fluids include, for example, 1,4 disubstituted semicarbazides such as 4-allyl-1-phenylsemicarbazide, 4-allyl-1-(2-bromophenyl)semicarbazide, 4-allyl-1-(2-chlorophenyl)semicarbazide, 4-allyl-1-(4-chlorophenyl)semicarbazide and 4-allyl-1-(4-methylphenyl)semicarbazide; thiosemicarbazides such as 4-allyl-1-(2-bromophenyl)thiosemicarbazide, 4-allyl-1-(2-chlorophenyl)thiosemicarbazide and 4-allyl-1-(4-chlorophenyl)thiosemicarbazide, as well as 1,5-disubstituted carbazides such as 1,5-diphenylcarbazide, 1,5-di-(4-methylphenyl)carbazide, 1,5-di-(4-bromophenyl)carbazide, 1,5-di-(4-chlorophenyl)-carbazide, 1,5-di-(2-chlorophenyl)carbazide and 1,5-di-(2-bromophenyl)carbazide.

Substances having peroxidative activity which are useful in the present invention can be selected from various organic and inorganic sources. Plant peroxidases, such as horseradish peroxidase or potato peroxidase and inorganic salts such as potassium iodate and sodium molybdate; small measured portions of whole blood, red blood cells alone, lyophylized blood, urohemin and other porphyrin substances having peroxidase activity can be used.

The method of practicing the present invention is further illustrated by the following examples which are provided to further demonstrate the method of practicing the invention and the advantages inherent therein and are not intended to limit the scope of the invention as claimed.

EXAMPLE I

Preparation of 1,4-Semicarbazide Derivatives

As starting material, 4-chlorophenylhydrazine hydrochloride (2.7 g, 15 mmole) in 100 mL of $H_2O$ was made basic with 10 N NaOH and extracted with $2 \times 75$ mL of ether. The ether extracts were dried ($MgSO_4$) and filtered. The ether solution of the free base was then cooled in an ice bath and an ether solution of allyl isocyanate (1.2 g, 15 mmole) was added slowly, resulting in precipitation of the product as a white solid which was collected and recrystallized from ethyl acetatehexane. Yield: 2.3 g (68%). IR ($CHCl_3$, cm-1) 1660 (C=O). Anal. Calcd. for $C_{10}H_{12}ClN_3O$: C, 53.22; H, 5.36; N, 18.62. Found: C, 53.46; H, 5.37; N, 18.73.

The compounds in Table 1 were prepared in a similar manner from the corresponding hydrazine hydrochloride or free base and isocyanate.

TABLE 1

$$R^1-NHNHCNHR^2 \; (\text{with } C=O)$$

| $R^1$ | $R^2$ | IR(Cm$^{-1}$) | m.p.(°C.) |
|---|---|---|---|
| $C_6H_5$ | $CH_3$ | 1683 | 149–50° |
| $C_6H_5$ | allyl | 1682 | 137–8° |
| $C_6H_5$ | $CH_2C_6H_5$ | 1683 | 128–9° |
| 4-$CH_3C_6H_4$ | allyl | 1659 | 160–1° |
| 4-$CH_3O-C_6H_4$ | allyl | 1659 | 144–5° |
| 4-Cl—$C_6H_4$ | allyl | 1659 | 159–60° |
| 2-$CH_3C_6H_4$ | allyl | 1661 | 115–6° |
| 2-Cl—$C_6H_4$ | allyl | 1680 | 85–8° |
| 4-$NO_2C_6H_4$ | allyl | 1632 | 198–9° |
| 3-$NO_2C_6H_4$ | allyl | 1633 | 147–8° |
| 4-$HO_2C-C_6H_4$ | allyl | 1681, 1651(sh) | 215–6°-a |
| 4-F—$C_6H_4$ | allyl | 1657 | 160–1° |
| 2-$NO_2C_6H_4$ | allyl | 1641 | 161–2° |
| 2-Br—$C_6H_4$ | allyl | 1671 | 111–2° |
| 3-Br—$C_6H_4$ | allyl | 1623 | 126–8° |
| 4-Br—$C_6H_4$ | allyl | 1657 | 155–7° |
| 2-F—$C_6H_4$ | allyl | 1660 | 105–6° |
| 2-$C_5H_4N$ | $CH_2C_6H_5$ | 1666 | 170° dec. | a - monohydrate

EXAMPLE II

Detection of 1–5q/dL Glucose in Urine Using a Polyurethane Matrix

A polyurethane matrix containing 3,3',5,5'-tetramethylbenzidine (TMB) was prepared by the method disclosed in U.S. Pat. No. 4,824,639 using the following materials: 3.67 g of powdered Dralon T ® polyacrylonitrile (Bayer AG), 65.2 g of a 20% (w/w) solution of Bayer AG KBH ® 776 polyurethane in dimethylformamide (DMF, Fluka), 86.6 g of a 25% (w/w) solution of Mowilith 50 ® polyvinylacetate (Hoechst) in DMF, and 22.5 g of sodium dodecyl sulfate (SDS, Serra) were added to 40 g of DMF. Next were added 37.1 g of $BaSO_4$, 37.1 g of Talkum ATl ® (Norwegian Talc), 12 g of TMB, and 17.3 g of Bayer AG KPK ® cationic polyurethane dispersion. Finally, 87.93 g of DMF was added and the resulting coating solution filtered through a 25μm mesh sieve. The viscosity of this coating solution was determined as 1850 cps at 20° C. The coating solution was then used to coat a 30 meter film of 150μm wet thickness on a Hostaphan RN 190 ® polyester (Hoechst) support. The coagulation bath temperature was 46° C. The wet polyurethane matrix was then dried to form a cohesive film. The polyurethane matrix described above was then coated with the following solutions and dried at 40° C. for 15 minutes.

| Solution 1 | |
|---|---|
| 1M citrate buffer, pH 5.0 | 20 mL |
| peroxidase (100 U/mg) | 1.0 g |
| glucose oxidase (100 U/mg) | 0.7 g |
| Triton X-100 ® | 1 mL |
| 1% FD&C yellow #5 solution | 1 mL |
| distilled water | adj 100 mL |
| Solution 2 | |
| 4-allyl-1-(4-chlorophenyl)semicarbazide | 2.82 g |
| 1-methoxy-2-propanol (MOP) | adj 100 mL |

To prepare the test devices, the coated polyurethane matrix was cut into a square measuring about 0.6 centimeter (cm) on a side, and mounted on one end of a polystyrene film strip measuring 0.6 × 10 cm. Mounting was accomplished through the use of double-sided adhesive available from the 3M Company.

A set of strips was dipped in urine samples containing 0, 1, 2, 3, and 5 g/dL glucose. The color formation of the strips was monitored instrumentally using a Macbeth Colorimeter (commercially available from Kollmorgen Corporation). This device is a scanning reflectance spectrophotometer suitable for the rapid measurement of reflectance spectra in the visual range, 400–700 nm. The reflectance data was used to calculate L*, a*, b* values and $\Delta E$ values between two samples. $\Delta E$ is a measure of the total color difference between two samples in three-dimensional color space. $\Delta E$ is calculated with the following equation [see D. B. Judd and G. Wyszecki; "Color in Business, Science, and Industry", John Wiley and Sons, New York (1975)]:

$$\Delta E = [(\Delta L^*)^2 + (\Delta a^*)^2 + (\Delta b^*)^2]^{\frac{1}{2}}$$

where $\Delta L^*$ is a measure of the difference in lightness between two samples, and varies from 0 for absolute black to 100 for perfect white; $\Delta a^*$ is a measure of the and $\Delta b^*$ is a measure of the difference in yellowness-blueness between two samples. Two colors are usually perceived as different by the human eye if the $\Delta E$ between them is at least three color difference units. For the test composition described earlier, absent the semicarbazide inhibitor, dipping the test device in urine samples containing 2 g/dL glucose or higher produced a dark blue-black color and no further color discrimination between higher glucose concentrations was observed. This dark color was found to correlate to a L* value of 30 units or below. Lighter and more visually-discernible colors were observed between different urine samples of lesser concentration of glucose that exhibited L* values above 30 units.

In order to illustrate the advantages of the invention, the test composition described earlier was prepared with and without the addition of the semicarbazide inhibitor. The results of the testing are presented in Table 2, wherein all results are expressed in L* and $\Delta E$ units.

TABLE 2

| Glucose Concentration (g/dL) | Without Semicarbazide L* Value | ΔE | With Semicarbazide L* Value | ΔE |
|---|---|---|---|---|
| 0 | 86.32 |  | 83.32 |  |
|  |  | 60 |  | 35 |
| 1 | 36.55 |  | 58.88 |  |
|  |  | 7 |  | 21 |
| 2 | 30.91 |  | 41.82 |  |
|  |  | 6 |  | 6 |
| 3 | 27.89 |  | 36.79 |  |
|  |  | 5 |  | 8 |
| 5 | 25.00 |  | 30.74 |  |

The instrumental data show that, in the absence of semicarbazide, the color differences between samples containing 2 g/dL glucose or above are not distinguishable visually due to low L* values (L*$_{2\ g/dL}$=30.91, L*$_{3\ g/dL}$=27.89, and L*$_{5\ g/dL}$=25.00), whereas in the presence of semicarbazide, the L* values are greater than 30 units for urine samples containing up to 5 g/dL glucose, with color development proceeding from a pale green to a dark blue-black. Color formation previously seen with glucose concentrations of 1 and 2 g/dL in test devices without semicarbazide is now exhibited with samples containing 3 and 5 g/dL glucose respectively. In addition, the ΔE between a negative sample and a sample containing 1 g/dL glucose has been reduced from 60 units to 35 units, a 42% decrease, and redistributed to subsequent glucose levels in the strips due to the semicarbazide, thereby enhancing the color differences observed between these urine samples.

EXAMPLE III

Detection of 1-5g/dL Glucose in Urine Using a Paper Matrix

Filter paper (Whatman 54) was impregnated, by immersion, with the following solutions and then dried at 50° C. for 10 minutes.

| Solution 1 | |
|---|---|
| 1M citrate buffer, pH 5.0 | 20 mL |
| peroxidase (100 U/mg) | 1.0 g |
| glucose oxidase (100 U/mg) | 0.7 g |
| Triton X-100 ® | 1 mL |
| distilled water | adj 100 mL |
| Solution 2 | |
| tetraethylbenzidine (TEB) | 2.96 g |
| 4-allyl-1-(4-chlorophenyl)semicarbazide | 2.70 g |
| ethylcellulose N50 | 0.5 g |
| toluene | 5.0 mL |
| 1-methoxy-2-propanol (MOP) | adj 100 mL |

The method for making the test devices was as described in Example II and testing of the devices was carried out, also as previously described, in urine samples containing 1 to 5 g/dL glucose. The L* and ΔE values obtained from this testing on the Macbeth Colorimeter are shown in Table 3.

TABLE 3

| Glucose Concentration (g/dL) | With Semicarbazide L* Value | ΔE |
|---|---|---|
| 0 | 89.69 |  |
|  |  | 32 |
| 1 | 69.20 |  |
|  |  | 13 |
| 2 | 59.25 |  |
|  |  | 8 |
| 3 | 51.49 |  |
|  |  | 5 |
| 5 | 46.89 |  |

As the instrumental results show, the color darkness has been reduced, as evidenced by the higher L* values. In the absence of semicarbazide in this test composition, the L* values for all the urine samples tested were below 35 units and visually indistinguishable. As in Example II, visually discernable colors were observed up to 5 g/dL glucose in the urine samples tested.

EXAMPLE IV

Detection of 0.1–1g/dL Glucose in Urine Using a Paper Matrix

Filter paper (Whatman BP87) was impregnated, by immersion, with the following solutions and dried at 60° C. for 18 minutes.

| Solution 1 | |
|---|---|
| 1, 2, 3, 4-butanetetracarboxylic acid | 14.0 g |
| N,N-bis[2-hydroxyethyl]-2-aminoethane sulfonic acid | 4.3 g |
| peroxidase (100 U/mg) | 125 mg |
| glucose oxidase (100 U/mg) | 300 mg |
| 0.1M sodium lauryl sulfate (SDS) | 0.5 mL |
| 0.1M FeHEDTA (hydroxyethylenediaminetriacetic acid), Ferric ion complex | 10 mL |
| potassium bromate | 1.25 g |
| distilled water | adj 100 mL |
| Solution 2 | |
| tetramethylbenzidine (TMB) | 2.41 g |
| 4-allyl-1-(4-chlorophenyl)semicarbazide | 0.23 g |
| ethyl acetate | adj 100 mL |

The method for making the test devices was as described in Example II. In addition to the test devices stored at ambient temperature, strips were also stored at 60° C. for one week in order to assess the storage stability, i.e. "shelf-life" under elevated temperature conditions. The test composition was also prepared as described above without the semicarbazide inhibitor for comparison purposes. Sets of strips stored under both ambient and 60° C. conditions were dipped in urine samples containing 0, 0.05, 0.1, 0.25, 0.5, and 1 g/dL glucose. The color formation of the strips was monitored instrumentally using a Macbeth Colorimeter. The results of this testing, expressed as L*, ΔL* and ΔE values, for both storage conditions are presented in Tables 4 and 5.

TABLE 4

| Glucose Concentration (g/dL) | Without Semicarbazide 7 Days at 23° C. L* Value | ΔE | 7 Days at 60° C. L* Value | ΔE | ΔL* |
|---|---|---|---|---|---|
| 0.00 | 83.69 |  | 80.28 |  | −3.41 |
|  |  | 36 |  | 20 |  |
| 0.05 | 53.78 |  | 71.08 |  | 17.30 |
|  |  | 14 |  | 12 |  |
| 0.10 | 48.78 |  | 63.16 |  | 14.38 |
|  |  | 10 |  | 13 |  |
| 0.25 | 40.68 |  | 54.62 |  | 13.94 |
|  |  | 5 |  | 7 |  |
| 0.50 | 35.77 |  | 49.04 |  | 13.27 |
|  |  | 1 |  | 3 |  |

TABLE 4-continued

| Glucose Concentration (g/dL) | Without Semicarbazide | | | | |
|---|---|---|---|---|---|
| | 7 Days at 23° C. | | 7 Days at 60° C. | | |
| | L* Value | ΔE | L* Value | ΔE | ΔL* |
| 1.00 | 35.52 | | 46.40 | | 10.88 |

TABLE 5

| Glucose Concentration (g/dL) | With Semicarbazide | | | | |
|---|---|---|---|---|---|
| | 7 Days at 23° C. | | 7 Days at 60° C. | | |
| | L* Value | ΔE | L* Value | ΔE | ΔL* |
| 0.00 | 82.52 | | 82.26 | | −0.26 |
| | | 3 | | 4 | |
| 0.05 | 81.04 | | 79.26 | | −1.78 |
| | | 10 | | 6 | |
| 0.10 | 77.35 | | 75.93 | | −1.42 |
| | | 18 | | 11 | |
| 0.25 | 64.26 | | 69.92 | | 5.66 |
| | | 6 | | 5 | |
| 0.50 | 60.09 | | 66.07 | | 5.98 |
| | | 6 | | 7 | |
| 1.00 | 56.17 | | 61.07 | | 4.90 |

The foregoing instrumental data confirm that test devices containing the semicarbazide inhibitor redistribute the visual color discrimination seen between a negative sample and the first analyte concentration of interest to subsequent glucose levels for low concentrations of analyte as well as high. These data illustrate the substantially increased stability of test devices containing the semicarbazide inhibitor under adverse storage and temperature "stress" conditions. Comparison of the ΔL* values of Tables 4 and 5 show a significantly smaller decrease in L* with storage under elevated temperature conditions for the test device which contained the inhibitor. The enhanced stability of the devices of the invention enabled them to detect the presence of glucose even after such "stress" conditions, whereas the degradation of the device without the inhibitor was comparatively more rapid and substantial as to render it much less reactive to glucose and therefore less desirable in terms of "shelf-life".

EXAMPLE V

Comparison of the Preferred Embodiment of the Invention with the Prior Art

A comparison of the preferred embodiment of the invention, 4-allyl-1-arylsemicarbazide derivatives, with the prior art, 1-phenylsemicarbazide, was done for the detection of 1–5 g/dL glucose in urine using a polyurethane matrix. Three cases were compared using the test composition, testing procedure, and evaluation described in Example II, with the exception that different semicarbazide inhibitors 1-phenylsemicarbazide (7.6 mg/mL) and 4-allyl-1-(2-chlorophenyl)semicarbazide (28.2 mg/mL), were used rather than the 4-allyl-1-(4-chlorophenyl)semicarbazide in the second solution. The storage conditions utilized in this comparison were the same as those outlined in Example IV. The results of this comparison, expressed in L*, ΔL* and ΔE values, are shown in Tables 6 and 7:

TABLE 6

| Glucose Level (g/dL) | Storage at Ambient Temperature for 3 Days | | | | | |
|---|---|---|---|---|---|---|
| | Case 1 | | Case 2 | | Case 3 | |
| | L* Value | ΔE | L* Value | ΔE | L* Value | ΔE |
| 0 | 86.32 | | 86.11 | | 84.44 | |
| | | 60 | | 12 | | 46 |
| 1 | 36.55 | | 78.92 | | 44.84 | |
| | | 7 | | 34 | | 11 |
| 2 | 30.91 | | 53.86 | | 35.75 | |
| | | 6 | | 13 | | 6 |
| 3 | 27.89 | | 42.90 | | 32.29 | |
| | | 5 | | 10 | | 4 |
| 5 | 25.00 | | 38.66 | | 30.86 | |

Case 1 = no semicarbazide
Case 2 = 7.6 mg/dL of 1-phenylsemicarbazide (50 mM)
Case 3 = 28.2 mg/dL of 4-allyl-1-(2-chlorophenyl)-semicarbazide (125 mM)

TABLE 7

| Glucose Level (g/dL) | Storage at 60° For 3 Days | | | | | | | | |
|---|---|---|---|---|---|---|---|---|---|
| | Case 1 | | | Case 2 | | | Case 3 | | |
| | L* Value | $^1\Delta L^*$ | ΔE | L* Value | $^1\Delta L^*$ | ΔE | L* Value | $^1\Delta L^*$ | ΔE |
| 0 | 82.50 | 3.8 | | 86.62 | −0.5 | | 84.79 | −0.4 | |
| | | | 56 | | | 37 | | | 47 |
| 1 | 38.01 | −1.5 | | 63.22 | 15.7 | | 44.74 | 0.1 | |
| | | | 10 | | | 16 | | | 12 |
| 2 | 29.83 | 1.1 | | 50.92 | 2.9 | | 35.33 | 0.4 | |
| | | | 6 | | | 17 | | | 5 |
| 3 | 28.50 | −0.6 | | 36.91 | 6.0 | | 32.27 | 0.0 | |
| | | | 1 | | | 10 | | | 6 |
| 5 | 28.02 | −3.0 | | 28.17 | 10.5 | | 29.21 | 1.7 | |

$^1\Delta L^*$ = L* (ambient temperature) −L* (3 days at 60°)

From this data it can be determined that Case 3 is superior to Cases 1 and 2 in the detection of 1–5g/dL glucose in urine in this test device. In comparison of Case 1 and Case 3, Case 3 is preferred because it provides good visual color discrimination between subsequent glucose levels up to 5g/dL glucose, as demonstrated by the L* values above 30 units, under both ambient and elevated temperature storage conditions. Addition of 4-allyl-1-(2-chlorophenyl)semicarbazide to the test composition resulted in a 23% decrease in the ΔE observed between a negative sample and one containing 1g/dL glucose [$\Delta E_{0\rightarrow 1}$ (case 1)=60 units v. $\Delta E_{0\rightarrow 1}$ (case 3) =46 units]. In Case 2, visually discernible were observed up to 5g/dL glucose, as evidenced by the L* and ΔE values. However, upon examination of the ΔL* values between ambient and elevated temperature storage conditions, frequently used to predict storage stability, i.e. "shelf-life", for Case 2, a significant loss of stability of the test device, demonstrated by significant changes in L* value, under adverse storage and temperature "stress" conditions was observed. In comparison, Case 3 exhibited virtually no change in L* value with storage under elevated temperature conditions for the test device, rendering it more desirable in terms of "shelf-life".

This procedure was repeated with various 1,4-di-substituted semicarbazides and carbazides. The results of these experiments are presented in Table 8. From Table 8 it can be determined that the percentage decrease in the ΔE between a negative sample and one containing 1 g/dL glucose relative to the control varied from about 80% for 1-phenylsemicarbazide to 3% for 4-allyl-1-(4-nitrophenyl)semicarbazide.

TABLE 8

Semicarbazide Solid Phase Results For High Range Urine Glucose

| Semicarbazide | L* Value₁ | ΔE₀→₁ | ΔE₁→₂ | ΔE₂→₃ | ΔE₃→₅ | % ΔE₀→₁[1] Reduced |
|---|---|---|---|---|---|---|
| Control | 36.55 | 59.9 | 7.1 | 6.0 | 4.7 | 0.0 |
| 1-Phenylsemicarbazide | 78.92 | 12.1 | 33.6 | 13.1 | 6.0 | 79.8 |
| 4-Methyl-1-phenylsemicarbazide | 66.26 | 26.1 | 25.7 | 14.4 | 7.5 | 56.4 |
| 4-Allyl-1-(4-methoxyphneyl)-semicarbazide | 57.75 | 26.4 | 17.5 | 10.2 | 7.3 | 55.9 |
| 1,5-Diphenylcarbazide | 59.46 | 27.9 | 18.8 | 7.0 | 5.1 | 53.4 |
| 4-Allyl-1-phenylsemicarbazide | 62.96 | 29.4 | 23.1 | 10.0 | 7.0 | 50.9 |
| 4-Benzyl-1-(2-pyridyl)-semicarbazide | 64.17 | 30.4 | 17.7 | 11.3 | 6.3 | 49.3 |
| 4-Phenyl-1-(2-pyridyl)-semicarbazide | 61.17 | 31.8 | 22.8 | 9.0 | 3.5 | 46.9 |
| 4-Allyl-1-(4-tolyl)semicarbazide | 53.25 | 32.6 | 17.1 | 8.0 | 6.0 | 45.6 |
| 4-Allyl-1-(4-bromophenyl)-semicarbazide | 61.01 | 32.7 | 17.9 | 9.9 | 8.6 | 45.4 |
| 4-Allyl-1-(4-fluorophenyl)-semicarbazide | 61.56 | 34.3 | 20.4 | 9.5 | 7.1 | 42.7 |
| 4-Allyl-1-(4-chlorophenyl)-semicarbazide | 57.70 | 37.0 | 22.9 | 10.0 | 3.8 | 38.2 |
| 4-Allyl-1-(3-bromophenyl)-semicarbazide | 57.67 | 38.5 | 15.5 | 7.6 | 7.2 | 35.7 |
| 4-Benzyl-1-phenylsemicarbazide | 53.16 | 40.7 | 15.9 | 9.1 | 6.0 | 32.1 |
| 4-Allyl-1-(2-tolyl)semicarbazide | 52.33 | 43.2 | 13.5 | 4.4 | 9.5 | 27.9 |
| 4-Allyl-1-(3-nitrophenyl)-semicarbazide | 50.44 | 49.5 | 10.6 | 6.9 | 7.9 | 17.4 |
| 4-Allyl-1-(2-fluorophenyl)-semicarbazide | 51.29 | 50.4 | 13.7 | 8.3 | 4.0 | 15.9 |
| 4-Allyl-1-(2-chlorophenyl)-semicarbazide | 45.93 | 51.8 | 14.7 | 7.4 | 3.3 | 13.5 |
| 4-Allyl-1-(2-bromophenyl)-semicarbazide | 46.91 | 52.3 | 11.2 | 4.7 | 5.0 | 12.7 |
| 4-Allyl-1-(4-nitrophenyl)-semicarbazide | 46.97 | 58.3 | 14.3 | 4.8 | 4.7 | 2.7 |

[1] percentage change in initial color produced between 0→1 g/dL relative to the control formulation without semicarbazides The semicarbazide and carbazide derivatives useful in the present invention contain the general arylhydrazide structure:

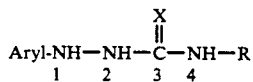

$$\text{Aryl-NH—NH—C(=X)—NH—R}$$
$$\quad\; 1 \quad\; 2 \quad\;\; 3 \quad\;\; 4$$

While we do not wish to be bound to any particular mechanism of how the invention operates, it is believed that these compounds act as competitive substrates with the chromogenic indicator in the reduction of activated peroxidase and in some cases may quench (reduce) the oxidized indicator with the N-1 electrons being the reducing species. The additive compound disclosed in U.S. Pat. No. 4,220,713, 1-phenylsemicarbazide is demonstrated in Tables 6 and 8 to be too potent in inhibiting color formation, particularly at low analyte levels. Another disadvantage of this material for this application is that the final, developed reaction colors in reagent systems containing it were not stable and faded within three minutes as evidenced by the data presented in Table 9. This is probably due to the reduction of the oxidized chromogen by the semicarbazide derivative.

Moderation of this color reduction property, leading to improved strip performance and thermal stability, was demonstrated by adding substituents, such as allyl, benzyl and methyl at the N-4 position. The reduced color inhibition is due to structural differences which affect either the enzyme substrate reactivity or reducing ability with the chromogen. However, developed color fading was also exhibited with many of the more potent members of this series, including 4-allyl-1-phenylsemicarbazide as shown in Table 9. Optimal performance is demonstrated by further elaboration of the 4-allyl-1-phenylsemicarbazide. Electron withdrawing group substitution on the N-1 phenyl decreases the availability of these electrons due to delocalization by resonance and inductive effects. This decreases the molecule's reducing ability thereby diminishing and moderating its color reducing and redistributing properties. In addition, developed colors using these phenyl-substituted derivatives were stable for up to 3 minutes, as shown in Table 9 and up to 5 minutes in subsequent formulations. In the extreme case of the strongly electron withdrawing 4-nitro group, the N-1 electrons are so delocalized into the aromatic nucleus that the semicarbazide no longer functions as a reducing agent and color redistributor.

TABLE 9

| Semicarbazide Derivative | ΔE₀→₁ g/dL | | Δ(ΔE₀→₁ g/dL) |
|---|---|---|---|
| | 2 minutes | 3 minutes | |
| 4-phenyl-1-(2-pyridyl)semi-carbazide | 32 | 20 | 12 |
| 4-allyl-1-phenylsemicarbazide | 29 | 18 | 11 |
| 4-methyl-1-phenylsemicarbazide | 26 | 19 | 7 |
| 4-allyl-1-(4-fluorophenyl)semicarbazide | 34 | 27 | 7 |
| 4-allyl-1-(4-chlorophenyl)semicarbazide | 35 | 31 | 4 |
| 1,5-diphenylcarbazide | 28 | 25 | 3 |
| 4-benzyl-1-phenylsemicarbazide | 41 | 38 | 3 |

TABLE 9-continued

| Semicarbazide Derivative | $\Delta E_{0 \to 1}$ g/dL 2 minutes | 3 minutes | $\Delta(\Delta E_{0 \to 1}\,g/dL)$ |
|---|---|---|---|
| 4-benzyl-1-(2-pyridyl)semicarbazide | 30 | 33 | 3 |
| 4-allyl-1-(2-fluorophenyl)semicarbazide | 50 | 48 | 2 |
| 4-allyl-1-(2-chlorophenyl)semicarbazide | 52 | 51 | 1 |
| 4-allyl-1-(4-methoxyphenyl)semicarbazide | 26 | 28 | 1 |
| 4-allyl-1-(4-bromophenyl)semicarbazide | 33 | 32 | 1 |
| 4-allyl-1-(2-bromophenyl)semicarbazide | 52 | 53 | 1 |
| 4-allyl-1-(4-tolyl)semicarbazide | 33 | 34 | 1 |
| 4-allyl-1-(2-tolyl)semicarbazide | 43 | 44 | 1 |

As previously mentioned, suitable color inhibitors for use in the present invention include 1,4-disubstituted semicarbazides, 1,4-disubstituted thiosemicarbazides and 1,5-disubstituted carbazides characterized by the formula:

$$\text{Aryl-NH—NH—}\overset{\overset{\displaystyle X}{\|}}{\text{C}}\text{—NH—R}$$

where X is oxygen or sulfur, R is alkyl, benzyl, aryl or NH-aryl$_2$. The aryl group can be a heteroaromatic moiety such as pyridine, thiophene, thiazole, quinoline, benzothiophene, benzothiazole, or a phenyl group which can be either unsubstituted or substituted with one or more moiety selected from the group consisting of alkoxy, aryloxy, alkyl, amido, alkylamido, arylamido, alkylthio, arylthio, carbamoyl, carbalkoxy, carboxyl, cyano, dialkylamino, halo, hydrogen, nitro, sulfo, sulfonamido, sulfamoyl, trialkylamino or ureido. These substituents can be ortho, meta or para to the semicarbazide N-1 nitrogen except in the case of the strongly electron withdrawing group —NO$_2$ which must be in the meta position to provide satisfactory results. Preferred electron withdrawing groups are methyl, chloro, bromo, fluoro, cyano, carboxyl and nitro.

Di- and tri- substitution of the aryl moiety is also contemplated. Thus 2,3-; 2,4-; 2,5-; 2,6- and 3,5- disubstituted aryl moieties, such as 4-allyl-1-(2,4-dibromo)-; 4-allyl-1-(2,5-dibromo)-; 4-allyl-1-(2-bromo-4-methoxy)-; 4-allyl-1-(4-chloro-2-methyl)and 4-allyl-1-(2-chloro-4-methyl)phenylsemicarbazide as well as trisubstituted aryl substituents such as, for example, 4-allyl-1-(2,6-dibromo-4-methyl)phenylsemicarbazide, 4-allyl-1-(2,4,6-tribromo)phenylsemicarbazide and 4-allyl-1-(4-chloro-2-methoxy-5-methyl)phenylsemicarbazide are suitable inhibitors for use in the present invention.

Also included within the scope of the present invention are certain novel 1,4-disubstituted semicarbazides which have demonstrated particularly desirable characteristics in terms of their ability to inhibit color intensity without causing rapid fading of the color developed by the indicator. In general, these are 1,4 semicarbazides which contain an allyl, alkyl of 1-6 carbon atoms or benzyl group at the 4- position and are substituted at the 1- position with an electron withdrawing aryl group such as a pyridyl group or a phenyl group bearing appropriate electron constituents. Typical of these semicarbazides are those set out in Table 9, wherein it is demonstrated that the stability of the color formed in the presence of these novel compounds is significantly greater than is the case with the prior art semicarbazides, such as 4-phenyl-1-(2-pyridyl)semicarbazide and 4-allyl-1-phenyl semicarbazide. Those semicarbazides and the carbazides which lie below 4-allyl-1-phenyl semicarbazide in Table 9 are claimed herein as compositions of matter due to their good activity as inhibitors of color formation which do not cause excessively rapid fading of the chromogen subsequent to its being oxidized to the colored form.

What is claimed is:

1. In a diagnostic reagent system for the detection of an analyte selected from the group consisting of glucose, cholesterol, triglyceride and uric acid consisting essentially of an oxidase selective for the analyte to be detected, a buffer, a chromogenic oxidation indicator which generates a colored response upon being oxidized together with peroxidase or a perioxidatively active substance, the improvement which comprises an inhibitor of color generation which is selected from the group consisting of 1,4-disubstituted semicarbazides, 1,4-disubstituted thiosemicarbazides and 1,5-disubstituted carbazides and thiosemicarbizides characterized by the formula:

$$\text{aryl-NH—NH—}\overset{\overset{\displaystyle X}{\|}}{\text{C}}\text{—NH—R}$$

where X is oxygen or sulfur, R is alkyl or 1-6 carbon atoms, allyl, benzyl, aryl or NH-aryl$_2$ where aryl$_2$ is the same as or different than aryl, which inhibitor reduces the intensity of the color generated by the oxidation of the chromogenic indicator thereby facilitating the visual and instrumental color discrimination between differing levels of analyte in the aqueous system.

2. The diagnostic reagent system of claim 1 wherein the peroxidase or peroxidatively active substance, chromogenic oxidation indicator and inhibitor of color generation are impregnated in a carrier matrix to provide a unitary testing device.

3. The diagnostic reagent system of claim 1 wherein the analyte is glucose, the peroxidatively active substance is horseradish peroxidase and the oxidase is glucose oxidase.

4. The diagnostic reagent system of claim 1 wherein the chromogenic oxidation indicator is benzidine or a substituted benzidine.

5. The diagnostic reagent systems of claim 4 wherein the chromogenic oxidation indicator is o-tolidine; o-dianisidine; 3,3',5,5'-tetramethylbenzidine; 3,3'-diaminobenzidine or 3,3'-dimethoxybenzidine.

6. The diagnostic reagent system of claim 1 wherein the inhibitor of color generation is a 1,4-disubstituted semicarbazide or thiosemicarbazide of the formula:

$$\text{aryl-NH—NH—}\overset{\overset{\displaystyle X}{\|}}{\text{C}}\text{—NH—R}$$

wherein aryl is a heterocyclic moiety, phenyl or substituted phenyl and R is alkyl of 1-6 carbon atoms, benzyl or allyl.

7. The diagnostic reagent system of claim 6 wherein aryl is substituted phenyl and R is methyl.

8. The diagnostic reagent system of claim 6 wherein X is oxygen.

9. The diagnostic reagent system of claim 8 wherein the inhibitor is 1,4-disubstituted semicarbazide or 1,5-disubstituted carbazide selected from the group consisting of: 4-methyl-1-phenylsemicarbazide; 4-allyl-1-(4-methoxyphenyl)semicarbazide; 1,5-diphenylcarbazide; 4-benzyl-1-(2-pyridyl)semicarbazide; 4-allyl-1-(4-bromophenyl)semicarbazide; 4-allyl-1-(4-fluorophenyl)semicarbazide; 4-allyl-1-(4-chlorophenyl)semicarbazide; 4-allyl-1-(3-bromophenyl)semicarbazide; 4-benzyl-1-phenylsemicarbazide; 4-allyl-1-(2-tolyl)semicarbazide; 4-allyl-1-(3-nitrophenyl)semicarbazide; 4-allyl-1-(2-fluorophenyl)semicarbazide; 4-allyl-1-(2-chlorophenyl)-semicarbazide; 4-allyl-1-(2-bromophenyl)semicarbazide or 4-allyl-1-(4-tolyl)semicarbazide.

10. The diagnostic reagent system of claim 6 wherein aryl is pyridyl, thienyl, thiazolyl, quinolinyl, benzothienyl, benthiazolyl or a substituted or unsubstituted phenyl group.

11. In a diagnostic reagent system for the detection of an analyte in an aqueous system which analyte is selected from the group consisting of glucose, cholesterol, triglyceride and uric acid which reagent system contains an oxidase specific for the analyte whose presence or concentration is being sought, a chromogenic oxidation indicator which generates a colored response upon being oxidized, a buffer and a peroxidase the improvement which consists essentially of the inclusion in such reagent system of an inhibitor of color generation which is a 1,4-disubstituted semicarbazide of the formula:

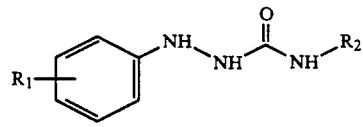

wherein $R_1$ is an electron withdrawing group and $R_2$ is allyl, benzyl, or alkyl of 1-6 carbon atoms.

12. The improvement of claim 11 wherein $R_1$ is alkoxy, aryloxy, alkyl, amido, alkylamido, arylamido, alkylthio, arylthio, carbamoyl, carbalkoxy, carboxyl, cyano, dialkylamino, halo, hydrogen, nitro, sulfo, sulfonamido, sulfamoyl, trialkylamino or ureido.

13. The improvement of claim 11 wherein $R_1$ is methyl, chloro, bromo, fluoro, cyano, carboxyl or nitro provided that when $R_1$ is nitro it is in the meta position.

14. The improvement of claim 11 wherein the inhibitor is 4-allyl-1-(2,4-dibromo)-, 4-allyl-1-(2,5-dibromo)-, 4-allyl-1-(2-bromo-4-methoxy)-, 4-allyl-1-(4-chloro-2-methyl), or 4-allyl-1-(2-chloro-4-methyl)phenylsemicarbazide.

15. The improvement of claim 11 wherein the inhibitor is 4-allyl-1-(2,6-dibromo-4-methyl), 4-allyl-1-(2,4,6-tribromo)-phenylsemicarbazide or 4-allyl-1-(4-chloro-2-methoxy-5-methyl)phenylsemicarbazide.

16. A diagnostic reagent system for the detection of glucose in an aqueous medium which reagent system comprises glucose oxidase, a buffer, a peroxidase and a substituted benzidine as chromogenic indicator together with a di-substituted semicarbazide of the formula:

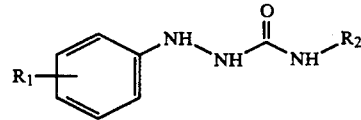

wherein $r_2$ is alkyl of 1-6 carbon atoms, allyl or benzyl and $R_1$ is an electron withdrawing group, said semicarbazide being present in sufficient amount to inhibit the color formed by oxidation of the substituted benzidiene to facilitate discrimination of the color intensity between different degrees of oxidation of the benzidine.

17. The reagent system of claim 1 wherein the benzidine indicator is 3,3',5,5' tetramethylbenzidine and the semicarbazide is 4-allyl-1-(2-chlorophenyl)semicarbazide.

18. A reagent pad for the detection of glucose in urine which comprises an absorbant support having absorbed therein glucose oxidase, a buffer, a peroxidase, a benzidine chromogenic indicator and 4-allyl-1-(2-substituted phenyl)semicarbazide.

19. The reagent pad of claim 18 wherein the indicator is 3,3',5,5 -tetramethylbenzidine and the semicarbazide is 4-allyl-1-(4-chlorophenyl)semicarbazide.

20. 1,4-disubstituted semicarbazide compounds of the formula:

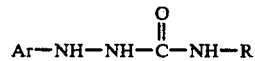

wherein R is alkyl of 1-6 carbon atoms, allyl or benzyl and Ar is an electron withdrawing heterocyclic compound or phenyl substituted with an electron withdrawing group.

21. The semicarbazides of claim 20 wherein Ar is pyridyl, thienyl, thiazolyl, quinolyl, benzothienyl or benzthiazolyl.

22. The semicarbazides of claim 20 wherein Ar is pyridyl.

23. The semicarbazides of claim 20 wherein R is methyl.

24. Semicarbazides of claim 209 selected from the group consisting of 4-methyl-1-phenylsemicarbazide, 4-allyl-1-(4-fluorophenyl)semicarbazide, 4-allyl-1-(4-chlorophenyl)-semicarbazide, 4-benzyl-1-phenylsemicarbazide, 4-benzyl-1-(2-pyridyl)semicarbazide, 4-allyl-1-(2-fluorophenyl)-semicarbazide, 4-allyl-1-(2-chlorophenyl)semicarbazide, 4-allyl-1-(4-methoxyphenyl)semicarbazide, 4-allyl-1-(4-bromophenyl)-semicarbazide, 4-allyl-1-(2-bromo-phenyl)semicarbazide, 4-allyl-1-(4-tolyl)semicarbazide, 4-allyl-1-(2-tolyl)-semicarbazide, 4-allyl-1-(3-bromophenyl)semicarbazide and 4-allyl-1-(3-nitrophenyl)semicarbazide.

* * * * *